United States Patent [19]
Mehl

[11] Patent Number: 5,964,691
[45] Date of Patent: Oct. 12, 1999

[54] COMPOSITION USEFUL FOR GELLED COSMETIC STICK

[75] Inventor: Nathan A. Mehl, Moore, S.C.

[73] Assignee: Milliken & Company, Spartanburg, S.C.

[21] Appl. No.: 08/905,057

[22] Filed: Aug. 1, 1997

[51] Int. Cl.$^6$ ................................................ B01J 13/00
[52] U.S. Cl. ............................ 516/20; 516/105; 514/940
[58] Field of Search ................ 424/65, 66; 514/940; 549/370, 433, 364, 372, 445, 453; 252/315.01, 315.1; 516/105, 20

[56] References Cited

U.S. PATENT DOCUMENTS

| | | | |
|---|---|---|---|
| 3,955,997 | 5/1976 | Sagane et al. | 106/148.5 |
| 4,722,835 | 2/1988 | Schamper et al. | 424/66 |
| 4,725,430 | 2/1988 | Schamper et al. | 424/66 |
| 4,781,917 | 11/1988 | Luebbe et al. | 424/65 |
| 4,816,261 | 3/1989 | Luebbe et al. | 424/65 |
| 5,106,999 | 4/1992 | Gardlik et al. | 549/364 |
| 5,200,174 | 4/1993 | Gardlik et al. | 424/66 |
| 5,286,755 | 2/1994 | Kauffmann et al. | 514/772 |
| 5,346,694 | 9/1994 | Juneja | 424/66 |
| 5,376,363 | 12/1994 | Benfatto et al. | 424/66 |
| 5,405,605 | 4/1995 | Shin | 424/68 |
| 5,490,979 | 2/1996 | Kasat et al. | 424/66 |
| 5,518,615 | 5/1996 | Vogler et al. | 252/315.1 |
| 5,609,855 | 3/1997 | Oh et al. | 424/65 |
| 5,643,866 | 7/1997 | Ansari et al. | 424/76.4 |
| 5,723,135 | 3/1998 | Ford et al. | 424/401 |

FOREIGN PATENT DOCUMENTS

| | | | |
|---|---|---|---|
| 2064179 | 3/1992 | Canada | A61K 7/32 |
| WO 91/15191 | 10/1991 | WIPO | A61K 7/38 |

*Primary Examiner*—Richard D. Lovering
*Assistant Examiner*—Daniel S. Metzmaier
*Attorney, Agent, or Firm*—Terry T. Moyer; Timothy J. Monahan

[57] ABSTRACT

A dispersion of dibenzylidene sorbitol acetal (DBS) in an organic liquid selected from alkylene glycols and polyalkylene glycols is provided wherein the DBS has a moisture content of greater than 2 wt. %, to inhibit the dispersion from gelling prematurely.

25 Claims, No Drawings

COMPOSITION USEFUL FOR GELLED COSMETIC STICK

BACKGROUND OF THE INVENTION

This invention relates generally to compositions containing an organic liquid and a sorbitol acetal gelling agent, which are useful in cosmetic sticks, such as antiperspirant and deodorant sticks. In particular, the invention relates to a stable dispersion of dibenzylidene sorbitol acetal (DBS) and a diol.

The use of DBS to gel organic liquids is well known. For example, DBS has been disclosed as a gelling or thickening agent for polyester (U.S. Pat. No. 3,767,729), hazardous liquids such as light oil (JP-B-77-043555), coal pitch or oil pitch (JP-B-77-028821), water and alcohol mixtures (JP-B-86-8695), and oil spills (U.S. Pat. No. 4,502,975).

The use of DBS to gel cosmetic stick compositions is also well known and exemplified in CA-A-2,064,179. Briefly, an astringent salt and/or an antibacterial agent are dissolved in a solvent, such as propylene glycol, along with DBS. Upon cooling, the DBS forms a network or matrix in the composition, causing the composition to gel.

In the manufacture of cosmetic sticks, it may be desirable to add the DBS to the composition in the form of a concentrated dispersion in an organic solvent. Since the dispersion must be pumped or poured, it is critical that it not gel or otherwise plug equipment and transfer lines. Consequently, there is an attendant risk in preparing concentrated dispersions of DBS in an organic solvent, that even under ambient conditions, the composition may gel, resulting in lost production.

Dibenzylidene sorbitols having various substituent groups on the aromatic rings, such as 1 to 3 alkyl or halo groups, are well known in the prior art and many are commercially available. The substituted DBS gelling agents and dibenzylidene sorbitol itself are referred to generally herein as "DBS compounds". DBS for use in gelling organic liquids is available under the trademark MILLITHIX 925® from the Milliken Chemical Division of Milliken & Company, Spartanburg, South Carolina. The product is sold with a specification of 1 to 2 wt. % water.

SUMMARY OF THE INVENTION

Therefore, an object of the invention is to provide a composition containing an organic liquid capable of being gelled by a DBS compound and a DBS compound dispersed therein, which may be used in the manufacture of cosmetic sticks. Another object of the invention is to provide a DBS/organic solvent composition which is stable for long periods of time, that is, pourable without gelling. Other objects of the invention include providing a concentrated composition containing 5 wt. % or greater of a DBS compound, a composition employing a $C_{2-6}$ dihydric alcohol or low molecular weight polyalkylene glycol as the gelling agent, and a means to stabilize a concentrated composition of a DBS compound without introducing additional compounds into the system.

Accordingly, a composition is provided of an organic liquid capable of being gelled by a DBS compound and 0.5 wt. % or more of a DBS compound dispersed in the liquid. The DBS compound has a water content of greater than 2 wt. %. The dispersion has the advantage of being stable for long periods of time, that is, it will not gel or set up, and remains pourable until the composition is ready to be used. The relatively high moisture content of the DBS compound does not adversely affect its gelling properties. For example, the composition can be heated and the DBS will dissolve in the organic liquid, and, upon cooling, precipitate in a network that creates a firm gel.

DETAILED DESCRIPTION OF THE INVENTION

Without limiting the scope of the invention, the preferred embodiments and features are hereinafter set forth. Unless otherwise indicated, all parts and percentages are by weight and conditions are ambient, i.e. one atmosphere of pressure and 25° C. The term "aromatic" refers to single and fused double-ring compounds having at least one unsaturated hydrocarbon ring. The term "aryl" refers to single and fused double-ring unsaturated hydrocarbons. Unless otherwise specified, aliphatic hydrocarbons are from 1 to 20 carbon atoms in length, and cycloaliphatic hydrocarbons comprise from 3 to 8 carbon atoms.

All of the United States patents cited in the specification are hereby incorporated by reference.

The composition of the present invention is a mixture of (a) an organic liquid capable of being gelled by a DBS compound; and (b) a DBS compound. The mixture is a dispersion, that is, only minor amounts of the DBS compound are soluble and dissolved in the organic liquid, with the bulk of the DBS compound being in the form of a particulate. Generally, the average particle size of the DBS compound will be in the range of about 50 to 200 microns or less.

The concentration of the DBS compounds in the composition is 0.5 wt. % or greater. Concentrations of the DBS compound as high as 40 wt. % or more may be employed, but approach the upper limit of solids concentration, viscosity and stability. Preferably, the concentration of DBS compound ranges from 5 to 30 wt. %, most preferably, 10 to 25 wt. %, based on the weight of the composition.

Organic liquids useful in the present invention are organic compounds and mixtures of organic compounds which are liquid at ambient conditions, and which are capable of being gelled by DBS compounds. In general, organic liquids in which a DBS compound has a solubility of about 0.5 g/100 g of solvent when heated, but is substantially less soluble in the solvent when cooled, are capable of being gelled. Virtually all common organic solvents which meet the aforementioned criteria may be employed. By way of example, the organic liquid may be selected from acetone, acetophenone, aniline, benzene, benzyl alcohol, n-butanol, carbon tetrachloride, castor oil, chlorobenzene, chloroform, coconut oil, cyclohexanone, dioctylphthalate, dioxane, epoxy resin (BPA type), ethanol, ethyl acetate, ethylene glycol, methyl ethyl ketone, nitrobenzene, octanol, propylene glycol, pyridine, tetraline, toluene, whale oil, xylene and liquid petroleum products, such as automotive and aviation fuel, fuel oil, illuminating oil, solvents (e.g. mineral spirits), lubricants, asphalts, cable oil and cutting oil.

In a preferred embodiment, the composition of the organic liquid and DBS compound is used as a concentrate in the manufacture of cosmetic sticks. Generally, the requirements of an organic liquid used in cosmetic sticks is that it be relatively non-toxic and compatible with the other ingredients. For example, the cosmetic stick may contain antiperspirants (astringents), antibacterials, fragrances, surfactants, emulsifiers, emollients, colorants, fillers, etc., as is known in the art. In most cases, the organic liquid will be a solvent for the antiperspirant ingredient. Suitable organic liquids may be generally classified as aliphatic alcohols, polyhydric alcohols and polyethers. For example, the organic liquid may be selected from $C_{2-6}$ alcohols and polyethers of $C_{1-4}$ alkylenes, including ethanol, n-propanol, n-butanol, t-butanol, isopropanol, isobutanol, 2-methoxyethanol, 2-ethoxyethanol, ethylene glycol, propylene glycol, e.g. 1,2-propylene glycol, 1,3-propylene glycol, butylene glycol, e.g. 1,4-butylene glycol, 1,3-butylene glycol, 1,2-butylene glycol, 2,3-butylene glycol, diethylene glycol monomethylether, diethylene glycol monoethylether, 2,4-dihydroxy-2-methylpentane, glycerine, pentylene glycols and hexylene glycol; and polyethylene glycols (e.g., diethylene glycol), polypropylene glycols (e.g., dipropylene glycol, tripropylene glycol) and polypropylene polyethylene glycol copolymers.

Preferably, the organic liquid is selected from $C_{2-6}$ dihydric alcohols such as ethylene glycol, 1,3-propylene glycol, 1,2-propylene glycol, 1,2-butylene glycol, 1,3-butylene glycol, 1,4-butylene glycol, 2,3-butylene glycol, 1,5-pentylene glycol and 1,6-hexylene glycol, and polyethylene glycols and polypropylene glycols having a molecular weight of 400 or less, such as diethylene glycol, dipropylene glycol and tripropylene glycol. Most preferably, the organic liquid is 1,2-propylene glycol. Those skilled in the art will recognize that the organic liquid may comprise mixtures of the aforementioned compounds and minor amounts of other miscible organic solvents, such as N-methyl-2-pyrrolidone or propylene carbonate, without deviating from the invention.

The term "DBS compound(s)" is intended to include dibenzylidene sorbitol acetal, as well as diacetals in general which are made by the condensation reaction between two moles of an aromatic aldehyde and one mole of a polyhydric alcohol. The aromatic aldehydes are single or fused double ring aldehydes having at least one unsaturated hydrocarbon ring, and include benzaldehyde, naphthaldehyde, indan aldehyde and tetrahydronaphthaldehyde (tetralin aldehyde). The aromatic aldehydes may be unsubstituted or have from one to five substituent groups selected from $C_{1-4}$ alkyl, $C_{1-4}$ alkoxy, hydroxy, halogen, $CH_2Cl$, $CH_2F$, $-CH=CHNO_2$, $C_{1-6}$ alkylthio, $C_{1-6}$ alkylsulfoxy, $C_{3-5}$ alkylene forming a carbocyclic ring with adjacent carbon atoms on an unsaturated hydrocarbon ring, carboxyl, ($C_1-C_{20}$ alkyloxy)carbonyl, ($C_1-C_{20}$ alkyloxy)ethyloxycarbonyl, ($C_1-C_{12}$ alkyl)phenyl, halogenated phenyl, ($C_1-C_{12}$ alkoxy)phenyl, ($C_1-C_{12}$ alkyloxy)ethyloxyethyloxycarbonyl and ($C_1-C_{12}$ alkyloxy)ethyloxyethyloxyethyloxycarbonyl groups. Preferably, the aromatic aldehyde is selected from unsubstituted benzaldehyde, benzaldehyde having from one to three substituent groups selected from $C_{1-4}$ alkyl, halogen and $C_{3-5}$ alkylene forming a carbocyclic ring with adjacent carbon atoms on an unsaturated hydrocarbon ring, including p-methyl, p-ethyl, 2,4-dimethyl, 3,4-dimethyl and 2,4,5-trimethyl benzaldehyde, 5-indan aldehyde and 5',6',7',8'-tetrahydro-2-naphthaldehyde. Preferred aromatic aldehydes are represented by the formula:

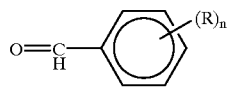

wherein n is 0, 1, 2 or 3, and R is independently selected from $C_{1-4}$ alkyl, halogen, or a three or four membered alkylene group forming a carbocyclic ring with adjacent atoms of the unsaturated parent ring.

Mixtures of the aromatic aldehydes may be provided and will result in a distribution of diacetals having the same or different aromatic components, referred to as symmetric and asymmetric diacetals, respectively. The aromatic aldehydes typically react with the polyhydric alcohol to form acetals in the 1:3 and 2:4 positions.

The polyhydric alcohols have five or more hydroxyl groups. The sugar alcohols represented by the formula $HOCH_2(CHOH)_nCH_2OH$, where n=3–5, have been found to be especially useful. Preferably, the polyhydric alcohol is a pentahydric or hexahydric alcohol, most preferably xylitol or sorbitol.

The DBS compound employed in the composition may be pure, or represent a mixture of DBS compounds.

Synthesis of the DBS compounds is typically conducted in a hydrophobic organic liquid medium in the presence of an acid catalyst, as is well known in the art, as shown by the following references: U.S. Pat. No. 3,721,682; U.S. Pat. No. 4,429,140; U.S. Pat. No. 4,902,807; and EP-B-0 497 976. Alternatively, the condensation reaction may be conducted in an aqueous medium as disclosed in U.S. Pat. No. 4,562,265 and U.S. Pat. No. 5,023,354. Diacetals of sorbitol and benzaldehyde and sorbitol and alkyl-substituted benzaldehyde are commercially available from Milliken Chemical, a division of Milliken & Company, Spartanburg, S.C., U.S.A.

Regardless of the medium used to synthesize the DBS compound, water is generated during the condensation reaction. Additionally, the reaction product is exposed to water during the work up step when the product is washed with water, leaving a moist filter cake. The water content of the filter cake may vary from process to process, but will generally be greater than 10 wt. % water, more typically 25 to 75 wt. % water.

The moist filter cake of the DBS compound may be dried in a heated agitated dryer under reduced pressure, as is commercially available for drying particulates.

It has been found that the gelling properties of the DBS compounds may be temporarily inhibited by drying the DBS compound to a point where it retains greater than 2 wt. % water, preferably 2.2 wt. % water or greater, most preferably, 2.4 wt. % water or greater. Excess water may adversely affect flow properties of the DBS compounds and it is generally not desirable to dilute the purity unnecessarily. Consequently, it is desirable to provide the DBS compound dried to a range of from greater than 2 wt. % to 4 wt. % water, preferably from 2.2 to 3.5 wt. % water, most preferably from 2.4 to 3.0 wt. % water.

Without being bound to a particular theory, it is believed that the water associated with the DBS compound is of two types: (a) "surface water" which is loosely associated with the surface of the particles and/or fills voids between the particles, and is removed relatively easy in the drying process; and (b) "bound water" which requires additional energy to remove during the drying process and is present in the interstices of the particle or as water of hydration within the DBS compound crystal structure.

The organic liquid/DBS compound composition may be formed by mixing the components in a conventional stirred vessel. It will generally be most convenient to mix the components and store the composition at ambient temperature. Nevertheless, the composition may be mixed and stored in a chilled vessel, for example at temperatures down to 3° C. or lower. Heating the composition is likely to promote dissolution of the DBS compound in the organic liquid, and gelation if the composition is cooled. Consequently, the composition is preferably not heated above about 70° C.

The advantage of the present invention is that the organic liquid/DBS composition may be stored for long periods of time without the necessity of heating or cooling the storage vessel. The composition is storage stable and will not gel at ambient temperatures, that is below 40° C., preferably below 35° C., even when held for long periods of time. The composition is stable for at least 24 hours, and at concentrations of the DBS compound at or below 30 wt. %, is stable for 480 hours or more.

The composition may also include various other ingredients used in cosmetic sticks. For example, the composition may include antiperspirants, such as aluminum or zirconium astringent salts, antibacterials, fragrances, surfactants, emulsifiers, emollients, colorants and fillers. The formulation of cosmetic sticks with DBS compounds as gelling agents is well known and may be found in the following references: WO-A-91/15191; CA-A-2,064,179; U.S. Pat. No. 4,722,835; U.S. Pat. No. 4,725,430; U.S. Pat. No. 4,781,917; U.S. Pat. No. 4,816,261; U.S. Pat. No. 5,200,174; U.S. Pat. No. 5,346,694; U.S. Pat. No. 5,376,363; U.S. Pat. No. 5,405,605; U.S. Pat. No. 5,490,979; U.S. Pat. No. 5,609,855.

In a preferred embodiment, the antiperspirants are dissolved separately in an organic liquid, such as propylene glycol. The organic liquid/DBS compound composition is then added as a concentrate to the antiperspirant solution to achieve a concentration of the DBS compound in the cosmetic stick of about 1 to 5 wt. %, preferably 2 to 4 wt. %.

The invention may be further understood by the following examples. Measurements of water content in the DBS samples were made using a Shimadzu moisture balance.

EXAMPLE 1

A 20 wt % dispersion was prepared by charging a 4 oz glass jar with 24.0 g of PG (propylene glycol) and 6.0 g DBS (dibenzylidene sorbitol) containing 2.6 wt % water. The jar was capped and then shaken vigorously for 30 seconds to ensure complete mixing of the materials. Initially, the mixture had the consistency of a thin milky dispersion. The mixture was periodically shaken and then tested for pourability. After 480 hours, the mixture was still pourable. The temperature during the experiment varied between 22° and 25° C.

EXAMPLE 2

A 20 wt % dispersion was prepared as in Example 1 using DBS containing 2.3 wt % water. The mixture was mixed and tested as in Example 1. After 480 hours, the mixture was still pourable. The temperature during the experiment varied between 22° and 25° C.

EXAMPLE 3 (Comparative)

A 20 wt % dispersion was prepared as in Example 1 using DBS containing 1.9 wt % water. The mixture was mixed and tested as in Example 1. After 0.8 hours, the mixture had thickened considerably and was no longer pourable. The temperature during the experiment was 23° C.

EXAMPLE 4 (Comparative)

A 20 wt % dispersion was prepared as in Example I using DBS containing 1.2 wt % water. The mixture was mixed and tested as in Example 1. After 0.3 hours, the mixture had thickened considerably and was no longer pourable. The temperature during the experiment was 23° C.

EXAMPLE 5

A 25 wt % dispersion was prepared by charging a 4 oz glass jar with 45.0 g of PG and 15.0 g DBS containing 2.6 wt % water. The jar was capped and then shaken vigorously for 30 seconds to ensure complete mixing of the materials. Initially, the mixture had the consistency of a thin milky dispersion. The mixture was periodically shaken and then tested for pourability. After 78 hours, the mixture was still pourable. The temperature during the experiment varied between 22° and 25° C.

EXAMPLE 6

A 30 wt % dispersion was prepared by charging a 4 oz glass jar with 42.0 g of PG and 18.0 g DBS containing 2.6 wt % water. The jar was capped and then shaken vigorously for 30 seconds to ensure complete mixing of the materials. Initially, the mixture had the consistency of a thin milky dispersion. The mixture was periodically shaken and then tested for pourability. After 24 hours, the mixture was still pourable. The temperature during the experiment varied between 22° and 25° C.

EXAMPLE 7

A 20 wt % dispersion was prepared by charging a 4 oz glass jar with 24.0 g of ethylene glycol and 6.0 g DBS containing 2.6 wt % water. The jar was capped and then shaken vigorously for 30 seconds to ensure complete mixing of the materials. Initially, the mixture had the consistency of a thin milky dispersion. The mixture was periodically shaken and then tested for pourability. After 24 hours, the mixture was still pourable. The temperature during the experiment varied between 22° and 25° C.

EXAMPLE 8 (COMPARATIVE)

A 20 wt % dispersion was prepared as in Example 7 using DBS containing 1.2 wt % water. The mixture was mixed and tested as in Example 7. After 0.1 hours, the mixture had thickened considerably and was no longer pourable. The temperature during the experiment was 23° C.

EXAMPLE 9

A 20 wt % dispersion was prepared by charging a 4 oz glass jar with 24.0 g of Diethylene Glycol and 6.0 g DBS containing 2.6 wt % water. The jar was capped and then shaken vigorously for 30 seconds to ensure complete mixing of the materials. Initially, the mixture had the consistency of a thin milky dispersion. The mixture was periodically shaken and then tested for pourability. After 24 hours, the mixture was still pourable. The temperature during the experiment varied between 22° and 25° C.

EXAMPLE 10 (COMPARATIVE)

A 20 wt % dispersion was prepared as in Example 9 using DBS containing 1.2 wt % water. The mixture was mixed and tested as in Example 9. After 0.1 hours, the mixture had thickened considerably and was no longer pourable. The temperature during the experiment was 23° C.

The results are summarized below in Table 1.

TABLE 1

Effect of Moisture Content on Gellation Time

| Example | Solvent | DBS Conc. (wt %) | $H_2O$ in DBS (%) | Gellation Time (hr) |
|---|---|---|---|---|
| 1 | Propylene Glycol | 20 | 2.6 | 480+ |
| 2 | Propylene Glycol | 20 | 2.3 | 480+ |
| 3 (comp.) | Propylene Glycol | 20 | 1.9 | 0.8 |
| 4 (comp.) | Propylene Glycol | 20 | 1.2 | 0.3 |
| 5 | Propylene Glycol | 25 | 2.6 | 78+ |
| 6 | Propylene Glycol | 30 | 2.6 | 24+ |
| 7 | Ethylene Glycol | 20 | 2.6 | 24+ |
| 8 (comp.) | Ethylene Glycol | 20 | 1.2 | 0.1 |
| 9 | Diethylene Glycol | 20 | 2.6 | 24+ |
| 10 (comp.) | Diethylene Glycol | 20 | 1.2 | 0.1 |

Example 1–10 demonstrate the dramatic effect that DBS water content has on the pourability of dispersions of DBS in various organic liquids. When DBS contains greater than 2% water (Examples 1 and 2) the dispersions of 20 wt % DBS in PG remain pourable for over 480 hours; however, when DBS contains less than 2% water (Examples 3 and 4), similar dispersions are no longer pourable after 0.8 and 0.3 hours, respectively. As the DBS concentration in the dispersion increases to 25 and 30 wt %, results from Experiments 5 and 6 clearly indicate that DBS with 2.6 wt % water allows the PG to remain pourable for greater than 24 hours.

Similar observations were made for dispersions of DBS in other organic liquids. In dispersions of 20 wt % DBS in both ethylene glycol and diethylene glycol, Examples 7–10 demonstrate that DBS containing 2.6 wt % water allows the mixture to remain pourable for greater than 24 hours, while DBS containing 1.2 wt % water leads to a thickened non-pourable gel in less than 0.1 hours.

There are of course, many alternative embodiments and modifications of the invention, which are intended to be included within the scope of the following claims.

What I claim is:

1. A pourable dispersion comprising a DBS compound dispersed in an organic liquid produced by the process of mixing from 10 to 40 wt. % of a DBS compound, said DBS compound having greater than 2 wt. % associated water and said water being sufficient to inhibit the dispersion from gelling, with an organic liquid capable of being gelled by the DBS compound, and said mixture forming a stable pourable dispersion of the DBS compound with the organic liquid for 24 hours at a temperature of 25° C.

2. The composition of claim 1 wherein the organic liquid is selected from the group consisting of $C_{2-6}$ alcohols and polyalkylene glycols of $C_{1-4}$ alkylenes.

3. The composition of claim 2 wherein the DBS compound is selected from the group consisting of diacetals which are the condensation product of an two moles of an aromatic aldehyde selected from the group consisting of benzaldehyde and benzaldehyde having from 1 to 3 substituent groups selected from $C_{1-4}$ alkyl, halogen, and $C_{3-5}$ alkylene forming a carbocyclic ring with adjacent carbon atoms on an unsaturated hydrocarbon ring, and one mole of a polyhydric alcohol selected from the group consisting of xylitol and sorbitol.

4. The composition of claim 6 wherein the DBS compound has greater than 2.4 wt. % associated water.

5. The composition of claim 4 wherein the composition comprises from 10 to 30 wt. % of the DBS compound and the composition.

6. The composition of claim 1 wherein the DBS compound is dibenzylidene sorbitol.

7. The composition of claim 6 wherein the DBS compound has from 2.2 to 3.5 wt. % associated water and comprises from 10 to 25 wt. % of the composition.

8. The composition of claim 6 wherein the DBS compound comprises from 10 to 30 wt. % of the composition.

9. The composition of claim 1 wherein the organic liquid is selected from the group consisting of ethylene glycol, propylene glycol, butylene glycol, diethylene glycol, dipropylene glycol and tripropylene glycol.

10. The composition of claim 9 wherein the DBS compound is dibenzylidene sorbitol and has greater than 2.2 wt. % associated water and the composition comprises from 10 to 30 wt. % of the DBS compound.

11. A composition comprising an organic liquid capable of being gelled, and 10 to 30 wt. % of a DBS compound dispersed in the organic liquid, wherein the DBS compound is selected from the group consisting of diacetals which are the condensation product of an two moles of an aromatic aldehyde selected from the group consisting of benzaldehyde and benzaldehyde having from 1 to 3 substituent groups selected from $C_{1-4}$ alkyl, halogen, and $C_{3-5}$ alkylene forming a carbocyclic ring with adjacent carbon atoms on an unsaturated hydrocarbon ring and one mole of a polyhydric alcohol selected from the group consisting of xyltiol and sorbitol, and the DBS compound is prepared by drying a slurry or filter cake of the DBS compound, having greater than 10 wt. % water, down to from 4 wt. % to greater than 2 wt. % associated water, and wherein the dispersion is pourable at 25° C.

12. The composition of claim 11, wherein the organic liquid is selected from the group consisting of ethylene glycol, propylene glycol, butylene glycol, pentylene glycol, hexylene glycol and polyalkylene glycols of $C_{1-4}$ alkylenes having a molecular weight of 400 or less.

13. The composition of claim 12, wherein the DBS compound is dibenzylidene sorbitol.

14. The composition of claim 13, wherein the organic liquid is 1,2-propylene glycol.

15. The composition of claim 14, wherein the DBS compound comprises from 10 to 25 wt. % of the composition, and the DBS compound is prepared by drying the slurry or filter cake down to from 2.2 to 3.5 wt. % associated water.

16. A method of making a pourable dispersion comprising the steps of dispersing from 10 to 40 weight % of a DBS compound, having greater than 2 weight % associative water and said water being sufficient to inhibit the dispersion from gelling, in an organic liquid capable of being gelled by the DBS compound, wherein the composition is a pourable dispersion for 24 hours at a temperature of 25° C.

17. The method of claim 16 wherein the organic liquid is selected from the group consisting of ethylene glycol, propylene glycol, butylene glycol, pentylene glycol, hexylene glycol and polyalkylene glycols of $C_{1-4}$ alkylenes having a molecular weight of 400 or less, and the dispersing temperature is less than 40° C.

18. The method of claim 17 wherein the DBS compound is selected from the group consisting of diacetals which are the condensation product of an two moles of an aromatic aldehyde selected from the group consisting of benzaldehyde and benzaldehyde having from 1 to 3 substituent groups selected from $C_{1-4}$ alkyl, halogen, and $C_{3-5}$ alkylene forming a carbocyclic ring with adjacent carbon atoms on an unsaturated hydrocarbon ring, and one mole of a polyhydric alcohol selected from the group consisting of xylitol and sorbitol.

19. The method of claim 18 wherein the DBS compound has from 2 wt. % and 4 wt. % associated water.

20. The method of claim 19 wherein the composition comprises from 10 to, 30 wt. % of the DBS compound and the composition.

21. The method of claim 16 wherein the DBS compound is dibenzylidene sorbitol.

22. The method of claim 21 wherein the DBS compound has from 2.2 wt. % and 3.5 wt. % associated water and comprises from 10 to 25 wt,% of the composition.

23. The method of claim 21 wherein the DBS compound comprises from 10 to 25 wt. % of the composition.

24. The method of claim 21, wherein the organic liquid is selected from the group consisting of the organic liquid is selected from the group consisting of ethylene glycol, propylene glycol, butylene glycol, diethylene glycol, dipropylene glycol and tripropylene glycol.

25. The method of claim 16 wherein the DBS compound has from 2.2 wt. % and 3.5 wt. % associated water and the composition comprises from 10 to 30 wt. % of the DBS compound.

\* \* \* \* \*

UNITED STATES PATENT AND TRADEMARK OFFICE
CERTIFICATE OF CORRECTION

PATENT NO.   : 5,964,691
DATED        : October 12, 1999
INVENTOR(S)  : Mehl, Nathan A.

Page 1 of 1

It is certified that error appears in the above-identified patent and that said Letters Patent is hereby corrected as shown below:

Column 8,
Line 4, after the word "claim" delete -- 6 -- and insert -- 3 --.

Column 9,
Line 12, after the word "to" delete -- , --.

Column 10,
Line 3, after the word "wt" delete -- , -- and insert -- . --.

Signed and Sealed this

Eighth Day of January, 2002

*Attest:*

*Attesting Officer*

JAMES E. ROGAN
*Director of the United States Patent and Trademark Office*